United States Patent
Rutledge et al.

(10) Patent No.: US 7,083,909 B2
(45) Date of Patent: Aug. 1, 2006

(54) COMPOSITION CONTAINING GAMETE OR EMBRYO AND ANIMAL WHITE YOLK AND THE USE THEREOF

(75) Inventors: Jackie J. Rutledge, Madison, WI (US); Mark E. Cook, Madison, WI (US); Ricky L. Monson, Madison, WI (US); Crague E. Cook, Madison, WI (US); Niels Jorgensen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/388,150

(22) Filed: Mar. 13, 2003

(65) Prior Publication Data

US 2003/0217380 A1 Nov. 20, 2003

Related U.S. Application Data

(60) Provisional application No. 60/417,213, filed on Oct. 8, 2002, provisional application No. 60/364,891, filed on Mar. 14, 2002.

(51) Int. Cl.
*A01N 1/02* (2006.01)
*C12N 5/06* (2006.01)

(52) U.S. Cl. .......................................... 435/2; 435/374

(58) Field of Classification Search .................... 435/2, 435/374, 1.1; 436/374, 2
See application file for complete search history.

(56) References Cited

OTHER PUBLICATIONS

Jeyendran et al. Human Reproduction Update. 1995. vol. 1, No. 1, pp. 73-79.*
Foulkes . J. Reprod. Fert. 1977, 49:277-284.*
Milovanov et al. Vestnik Sel'skokhozyaistvennoi Nauki. 1988, 4:138-139.*

Burley, R.W. and D.V. Vadehra. 1989. The Avian Egg. Chemistry and Biology. J. Wiley and Sons, N.Y., pp. 232-233.
Callebaut, M., E.V. Van Nueten, F. Harrison and H. Bortier 2000. Activation of avian embryo formation by unfertilized quail germ discs: comparison with early amphibian development. Reproduction, Nutrition, Development 40:597:606.
Hughes, R.L. and L.S. Hall, 1998 Early development and embryology of the platypus. Trans Roy. Soc. Lond. B. 353: 1101-1114.
Lillie, F. R. 1919. The Development of the Chick. An Introduction to Embryology. Henry Holt and Co., N.Y. pp. 20-43.
Marza, V.D., and E.V. Marza 1935. The formation of the hen's egg. Quart. Jour. Micros. Sci., 78:133-189.
Tanabe, Y, Sonoda, Y, Kai, O. and Imai, K. 2000. Changes in yolk sphere formation of ovarian follicles relating to the follicular transformation in laying hens (Translated title). Abstract Jap Poul Sci 37:306-309.
Middle School Science Project Leads to Frozen Poultry Semen Patent, May 9, 2002.
Burley, R.W. and D.V. Vadehra. 1989. The Avian Egg. Chemistry and Biology, J. Wiley and Sons, N.Y.
Lillie, F. R. 1919. The Development of the Chick. An Introduction to Embryology. Henry Holt and Co., N.Y.
Tanabe, Y, Sonoda, Y, Kai, O. and Imai, K, 2000. Changes in yolk sphere formation of ovarian follicles relating to the follicular transformation in laying hens (Translated title). Abstract Jap Poul Sci 37:306-309.
Middle School Science Project Leads to Frozen Poultry Semen Patent, May 9, 2002.

* cited by examiner

*Primary Examiner*—Vera Afremova
(74) *Attorney, Agent, or Firm*—Quarles & Brady LLP

(57) ABSTRACT

A composition that contains a gamete or an embryo and animal white yolk is disclosed. Also disclosed are applications of the composition.

5 Claims, No Drawings

COMPOSITION CONTAINING GAMETE OR EMBRYO AND ANIMAL WHITE YOLK AND THE USE THEREOF

CROSS-REFERENCE TO RELATED APPLICATIONS

This application claims the benefit of U.S. provisional application No. 60/364,891, filed on Mar. 14, 2002, and U.S. provisional application No. 60/417,213, filed on Oct. 8, 2002.

STATEMENT REGARDING FEDERALLY SPONSORED RESEARCH OR DEVELOPMENT

The invention was made with US Government support awarded by United States Department of Agriculture Grant No. 00-CRHR-0-6055. The United States Government has certain rights in this invention.

BACKGROUND OF THE INVENTION

The gene pool of various animals can be maintained either by collecting, breeding and housing the animals or by preserving the gametes (sperm and oocytes) or embryos in vitro. The latter method is more flexible and usually more cost-effective as well. In vitro gamete and embryo preservation has also been used in connection with in vitro cultures of gametes and embryos to reproduce human and non-human animals. For example, in in vitro fertilization (IVF) for the mammalian species, the collected sperm and oocytes are preserved and cultured in vitro before the oocytes are fertilized. After fertilization, the resultant embryos are cultured in vitro until a certain stage of maturity (usually blastocysts) is reached, after which the embryos are implanted to induce pregnancy.

The in vitro preservation and culture of gametes and embryos has been used more successfully in some species than in others. A freeze-thaw cycle reduces the percentage of viable sperm more dramatically in avian semen samples than in mammalian semen samples. On a related note, the freeze-thaw process can also reduce the percentage of viable oocytes and embryos. The frequency of productive pregnancy induced in bovines is 80% lower when the in vitro fertilized embryos implanted were frozen and thawed before being implanted. In addition, mammalian embryos are very sensitive to temperature change. For example, less than one-half of a degree temperature change can kill a mammalian embryo. In contrast, natural bird embryos, which are natively in contact with white yolk, are fairly resistant to temperature change (e.g., fertilized chicken eggs can be held at 32° F. for 10 hours without significant effect on hatching rate).

Moreover, IVF pregnancies also yield offspring having a higher rate of abnormalities than natural pregnancies. IVF procedures have yielded larger bovine calves and smaller human babies at a much higher frequency than natural pregnancies. These abnormalities may arise from poorly characterized differences between the environments encountered in vivo and in vitro by gametes and embryos. Also, many supplements of conventional culture systems do not naturally contact embryos in vivo during early embryo development. More particularly, the proteins encountered by gametes and embryos in vitro (e.g., bovine serum albumin, amniotic fluid and fetal calf serum) come from fully formed individuals that have homeostatic organs and adaptations to handle waste, control pH, transport food, and accommodate temperature insult.

In birds, reptiles, marsupials and egg-laying mammals such as monotremes (Hughes and Hall, 1998), natural embryos are in contact with white yolk, a minor egg yolk constituent (less than 2%) that differs in composition, structure, and physical properties from yellow yolk (Burley and Vadehra, 1989). White yolk, but not yellow yolk, contacts the early embryo and there is no clear demarcation between embryo and white yolk (Lillie, 1919) because of the meroblastic cleavage wherein some of the developing cells appear to have no membrane between the cytoplasm and the white yolk.

Growth of the avian ovum is known as vitellogenesis. As in most mammals, an avian chick has its full complement of oocytes at hatching. Marza and Marza (1935) divided oogenesis in the hen into three phases. The first, which can last for several years, is a quiescent period in which the primordial yolk is laid down and maintained. White yolk slowly accumulates in the second period, which lasts for about 2 months. In the final phase, which lasts for 5–9 days just prior to ovulation, yellow yolk is rapidly deposited.

White yolk surrounds and appears to compartmentalize yellow yolk. From a bulb-shaped white yolk latebra at the center of the egg yolk, an elongated stem extends toward the blastoderm if an embryo is present (or toward the blastodisc if the egg is unfertilized or if embryogenesis did not commence). The stem flares out at its distal end into the Nucleus of Pander. Contiguous with the Nucleus of Pander is a small amount of white yolk lying just below the vitelline membrane. Fabian (1982) determined that the Nucleus of Pander was directly over the center of the yolk in 90% of 181 White Leghorn eggs examined. Romanoff and Romanoff (1949) identified light colored rings within the mass of yellow yolk as white yolk, but these rings are not white yolk. Rather, these rings should be called light yolk as they are identical to yellow yolk except for color and probably reflect some diurnal aspect of yellow yolk deposition (Gilbert, 1971; Burley and Vadehra, 1989).

Yellow yolk protein and lipid are synthesized in the liver and then are transported via circulation to the ovary (Burley and Vadehra, 1989). White yolk generally has a non-liver origin. White yolk remains liquid after a freeze-thaw cycle whereas yellow yolk becomes firm and gelatinous, a change known as yolk gelling (Burley and Vadehra, 1989). Tanabe-Yuji et al. (2000) determined that 14 hours after oviposition one small white follicle of the ovary has a layer of yellow yolk spheres deposited just under the perivitelline membrane. Such follicles are called transition follicles. A hen in lay has a series of developing follicles from small white follicles to one the size of a laid egg.

White yolk can be collected in at least two ways. It can be separated from yellow yolk after one or more freeze-thaw cycles. It can also be collected from small immature follicles (diameter between 1 and 8 mm) where yellow yolk has not been deposited.

SUMMARY OF THE INVENTION

The present invention is summarized in that animal white yolk can be included in an in vitro composition in which a gamete or embryo is kept for the purpose of keeping the gamete or embryo alive, inducing the gamete to proliferate or mature, inducing the embryo to mature, fertilizing an oocyte, or a combination of any of the forgoing.

In one aspect, the present invention relates to a composition that contains a gamete or embryo and isolated animal white yolk.

In another aspect, the present invention relates to a method for keeping a gamete or embryo alive in vitro. The method involves mixing the gamete or embryo with animal white yolk.

In another aspect, the present invention relates to a method for culturing a gamete or embryo in vitro. The method involves maintaining the gamete or embryo in a culture medium that contains animal white yolk.

In another aspect, the present invention relates to a method for fertilizing an oocyte in vitro. The method involves maintaining an oocyte and a sperm cell in a fertilization medium that contains animal white yolk under suitable IVF conditions.

BRIEF DESCRIPTION OF SEVERAL VIEWS OF THE DRAWINGS

Not applicable.

DETAILED DESCRIPTION OF THE INVENTION

As used herein, the term "embryo" means a vertebrate at a pre-birth or pre-hatching stage of development. A fertilized oocyte is considered to be an embryo.

The term "isolated white yolk" means white yolk isolated from its in vivo natural environment. Complete purification is not required. The white yolk can be isolated and purified from normally associated material such that in the purified preparation the white yolk is the predominant component in the preparation. At the very least, the degree of purification is such that the extraneous material in the preparation does not interfere with use of the white yolk in the manner disclosed herein.

A gamete culture means a culture of gametes for the purpose of keeping the gametes alive, inducing the gametes to proliferate, inducing the gametes to mature, or a combination of any of the forgoing. An embryo culture means a culture of embryos for the purpose of keeping the embryos alive, maturing the embryos (e.g., from a fertilized oocyte to a blastocyst), or both.

It is disclosed here that white yolk from an egg-laying animal can be used as part of a medium for keeping the gamete or embryo alive in vitro, inducing the gamete to proliferate or mature in vitro, inducing the embryo to mature in vitro, fertilizing an oocyte in vitro, or a combination of any of the foregoing. When provided in a medium for culturing gametes or embryos, or for fertilizing an oocyte, animal white yolk can supplement or substitute for protein sources in the medium such as bovine serum albumin, fetal calf serum and others.

Advantageously, the risk to the embryo of pathogen-associated infection in gamete or embryo culture or in an IVF medium, and the risk to the surrogate mother, can be reduced when white yolk from an animal of a different taxonomic order is employed in the medium. Also, embryos cultured in animal white yolk can be more "in vivo-like" because white yolk is more likely than serum to provide the poorly-characterized embryotrophic and other factors important for embryo development and survival. For example, during typical IVF processes, microinjection of bovine and other embryos is difficult because the zona pellucida that surrounds the embryos become fairly rigid. Embryos cultured in animal white yolk, however, resemble in vivo embryos that are much less rigid and are easier to microinject. Furthermore, white yolk may reduce the risk of developmental abnormalities.

In addition, the use of bird white yolk may improve the adverse effects of temperature change on cultured embryos.

In one aspect, the present invention relates to a method for keeping a gamete or embryo alive in vitro during any handling or storing process. The method involves mixing the gamete or embryo with animal white yolk either directly or in a fluid having an osmotic pressure that does not disrupt the gamete or embryo. One of ordinary skill in the art is familiar with these fluids. Examples of such fluids include but are not limited to phosphate-buffered saline and many cell culture media.

In another aspect, the present invention relates to a method for culturing gametes or embryos in vitro. The method involves culturing gametes and embryos in a medium that contains animal white yolk. A skilled artisan is familiar with the media that can be used for culturing gametes or embryos. All of these media can be supplemented with, or a protein source therein can be substituted by, animal white yolk for use in the method of the present invention.

In another aspect, the present invention relates to a method for fertilizing an oocyte in vitro. The method involves maintaining the oocyte and a sperm cell in a fertilization medium that contains animal white yolk under suitable IVF conditions. A skilled artisan is familiar with the media that can be used for IVF. All of these media can be supplemented with, or a protein source therein can be substituted by, animal white yolk for use in the method of the present invention.

White yolk of any white yolk-producing species can be used in the above methods of the present invention for gametes or embryos of either the same or a different species. Species that are known to have white yolk structure include birds, reptiles, marsupials and egg-laying mammals such as monotremes (Hughes and Hall, 1998). Avian white yolk is a preferred white yolk and chicken white yolk is the most preferred white yolk for the purpose of the present invention.

For relatively long term cryogenic storage, the mixture of gametes and white yolk, or embryos and white yolk, can be cooled to a temperature below the body temperature of the donor animal and preferably below the freezing point of the mixture. Examples of temperatures at or below about which the mixture is stored include but are not limited to 4° C., −20° C. and −79° C. The term "about" used herein is meant to cover temperatures that slightly deviate from but retain the essential function of the recited temperature. The frozen mixture can be thawed as needed at a suitable temperature, examples of which include but are not limited to room temperature and 37° C. Other suitable thawing methods known to one of ordinary skill in the art can also be used. Sperm that are stored and thawed this way preferably have a viability rate of at least 80%, 90%, or 95%. The viability rate is defined as the number of viable sperm upon thawing divided by the total number of sperm in the frozen mixture times one hundred.

As an example, the present invention finds utility in a cattle reproduction process that involves IVF. White yolk can be used in one or more steps of the following cattle reproduction procedure which includes collecting immature cattle eggs, allowing the eggs to mature in vitro in a hormone-enriched medium, incubating matured eggs with sperm for 24 hours in an IVF medium (e.g., IVF-TL solution, catalog number BSS-010-D made by Specialty Media, 580 Marshall Street, Phillipsburg, N.J. 08865), washing away excess sperm and accessory cells, culturing fertilized eggs for 7 days, and implanting the embryos.

The white yolk for use in the present invention can be collected by any known method from either or both of a small immature follicle and a matured ovum. To collect white yolk from an immature follicle, a female donor animal is euthanized and its ovaries are exposed. Next, follicles with yellow yolk are removed and the content of immature follicles is extracted using, e.g., a syringe. Alternatively, a fully developed egg is frozen and cut in half. As egg yolk starts to warm, white yolk in the center thaws while yellow yolk remains as a gel. The liquid white yolk can be collected by aspiration. If not taken for immediate use, harvested white yolk can be stored at about 4° C. or lower, preferably at about −20° C. or lower. When ready for use, white yolk can be thawed and then mixed with gametes or embryos according to the invention.

Various mixtures containing a gamete or embryo and isolated white yolk as described above, including those that are frozen or thawed, are within the scope of the present invention.

EXAMPLE 1

White yolk from immature white follicles was harvested from a laying hen and was frozen at −20° C. for two days. Rooster semen was collected and diluted 1:100 with phosphate buffered saline (PBS). Semen viability was determined via microscopy. White yolk was thawed at room temperature and viable sperm in PBS were added to the thawed white yolk in the following volume/volume ratios of white yolk/diluted rooster semen: 1/8, 2/8, 3/8, 4/8, 5/8, 6/8, 7/8, 8/8 and 9/8. A control vial contained untreated, diluted semen. Vials with treated and untreated semen were frozen at −79° C. Semen was then thawed at room temperature and examined for percent viability via microscopy. Only 4% of the sperm in the control group were viable. Viable sperm in the white yolk group ranged from 80% (1/8 dilution) to 99% (9/8 dilution).

EXAMPLE 2

Bovine embryos were produced in vitro and cultured in a commercially available culture medium (Synthetic Oviductal Fluid catalog number BSS-046-D made by Specialty Media, Division of Cell & Molecular Technologies, Inc., 580 Marshall Street, Phillipsburg, N.J.) at 39° C., 5% $CO_2$ in air with a relative humidity of 95%. On day 5 of embryonic development (fertilization=day 0), the bovine embryo culture was supplemented with either fetal bovine serum or chicken egg white yolk at a concentration of 10%. One hundred and eighty-eight putative zygotes were represented in each group and were evaluated on days 6, 7 and 8 for development. On day 6, embryos supplemented with serum developed to blastocyst at a rate of 11% whereas the white yolk group developed at 5%. However, by day 7, which is considered to be the general morphological standard for blastocoele development in the bovine, each group showed 16% development to blastocyst. By day 8 each group remained similar with a final percentage of development to blastocyst at about 30%. Fetal calf serum is thought to have some agent which may cause premature blastocoele development whereas embryos cultured with egg white yolk showed a more "in vivo like" development.

EXAMPLE 3

About 1,200 bovine oocytes were matured and fertilized as described in First, N. L. and Parrish J. J. (1987). The medium employed for INF was the IVF-TL solution, catalog number BSS-010-D made by Specialty Media, 580 Marshall Street, Phillipsburg, N.J. 08865. The embryos were then cultured as described in Example 2.

On day 5 of embryonic development (fertilization=day 0), the bovine embryo culture was supplemented with fetal calf serum (the FCS group), chicken white yolk (the WY group) or nothing (the control group). Embryo yields on day 8 of embryonic development (the number of blastocysts present at the time of observation divided by the number of putative zygotes committed to culture) were 79/305 (26%), 160/462 (35%) and 134/426 (31%) for the control, FCS and WY groups, respectively ($P<0.05$).

Randomly selected grade 1 and 2 embryos (according to the standard set by the International Embryo Transfer Society—IETS) that reached blastocyst stage on day 7 were cryopreserved in a standard glycerol freezing medium (Em-Care, Aukland, NZ) and later thawed as described in Wilmut, I. (1986). Once thawed, the embryos were returned to and cultured in fresh culture medium (as described in Example 2) of the same type as that before cryopreservaton (control, FBS supplemented or WY supplemented). While in culture, those embryos that returned to the morphological stage and quality as they were at the time of cryopreservation were determined to be viable (survived). The escape of embryonic contents from the zona pellucida (outer glycoprotein shell/membrane) was used as the marker for hatching. The cumulative number and percentage of embryos that survived and hatched 72 hours after returned to culture upon thawing are shown in Table 1 below.

TABLE 1

| Characteristic | Control | FCS | WY |
| --- | --- | --- | --- |
| # thawed | 32 | 89 | 70 |
| # survived | 18 (56%)[1] | 29 (33%)[1] | 22 (31%)[1] |
| # hatched | 11 (61%)[1] | 16 (55%)[1] | 11 (50%)[1] |

[1]% and p > 0.25.

REFERENCES

All of which are herein Incorporated by Reference in their Entirety

Burley, R. W. and D. V. Vadehra. 1989. The Avian Egg. Chemistry and Biology. J. Wiley and Sons, N.Y.

Fabian, G. 1982. Shape and position of the latebra in the chicken egg. (Translated title). Zeitschrift fuer Angewandte Zoologie 69: 429–442.

First, N. L. and Parrish J. J. 1987. In vitro fertilization of ruminants. Journal of Reproduction and Fertility Suppl. 34: 151–165.

Gilbert, A. B. 1971. The egg: its physical and chemical aspects. In Physiology and Biochemistry of the Domestic Fowl. Bell, D. J. and B. M. Freeman Eds. Academic Press, New York and London.

Hughes, R. L. and L. S. Hall. 1998 Early development and embryology of the platypus. Trans Roy. Soc. Lond. B. 353: 1101–1114.

Lillie, F. R. 1919. The Development of the Chick. An Introduction to Embryology. Henry Holt and Co., N.Y.

Marza, V. D., and E. V. Marza 1935. The formation of the hen's egg. Quart. Jour. Micros. Sci., 78:133–189.

Romanoff, A. L. and A. J. Romanoff. 1949. The Avian Egg. John Wiley and Sons, NY Tanabe, Y, Sonoda, Y, Kai, O. and Imai, K. 2000. Changes in yolk sphere formation of ovarian follicles relating to the follicular transformation in laying hens (Translated title). Jap Poul Sci 37: 306–309.

Wilmut, I. 1986. Cryopreservation of mammalian eggs and embryos. In: Gwatin, R. B. L. (ed) Developmental Biology, Vol. 4, Manipulation of Mammalian Development. Plenum Press, London, pp. 217–247.

We claim:

1. A method for keeping a gamete alive in vitro comprising the step of:

harvesting white yolk from immature follicles of an avian animal where yellow yolk has not been deposited; and mixing the gamete with the harvested white yolk to form a mixture of the gamete and the white yolk.

2. The method of claim 1 wherein the gamete is a sperm cell.

3. The method of claim 1 wherein the gamete is an oocyte.

4. The method of claim 1 further comprising the step of:

cooling the mixture to a temperature below the body temperature of the white yolk donor animal.

5. The method of claim 1 further comprising the step of:

cooling the mixture to a temperature at which the mixture freezes.

* * * * *